United States Patent [19]

Groutas

[11] Patent Number: 4,929,736
[45] Date of Patent: May 29, 1990

[54] LATENT ISOCYNATE DERIVATIVES USEFUL FOR DEACTIVATING ENZYMES

[75] Inventor: William C. Groutas, Wichita, Kans.

[73] Assignee: Board of Trustees of the Wichita State University, Wichita, Kans.

[21] Appl. No.: 117,531

[22] Filed: Nov. 6, 1987

Related U.S. Application Data

[63] Continuation-in-part of Ser. No. 756,252, Jul. 18, 1985, abandoned.

[30] Foreign Application Priority Data

Jul. 17, 1986 [CA] Canada ................................. 514030
Jul. 18, 1986 [JP] Japan ................................. 61-168235

[51] Int. Cl.$^5$ ......................................... C07D 233/54
[52] U.S. Cl. ................................. 548/341; 514/335;
514/346; 514/396; 514/399; 514/423; 514/546;
514/576; 546/243; 546/262; 548/530; 560/12;
560/149; 562/430
[58] Field of Search ......................................... 548/341

[56] References Cited

PUBLICATIONS

Groutas et al., "Journal of Medicinal Chemistry", 28(2), pp. 204–209, 1985.

Primary Examiner—Glennon H. Hollrah
Assistant Examiner—Ba K. Trinh
Attorney, Agent, or Firm—Lowe, Price, LeBlanc, Becker & Shur

[57] ABSTRACT

Certain amino-acid derivatives are disclosed as effective inhibitors of human leukocyte elastase and therefore useful in preventing the imbalance of this proteolytic enzyme in vivo. The compounds specifically are derivatives L-valine, L-norvaline, L-norleucine, and L-methionine methyl ester azolides succinimides or pyridones and sulfonate salts, and related compounds such as L-leucine and L-phenylalanine methyl ester derivatives. The compounds were found to be excellent inhibitors in that they embody both inhibitory and anti-oxidant or anti-inflammatory activity.

1 Claim, No Drawings

LATENT ISOCYNATE DERIVATIVES USEFUL FOR DEACTIVATING ENZYMES

This application is a continuation-in-part of my patent application Ser. No.: 756,252 filed July 18, 1985, now abandoned.

This invention relates to the discovery that certain latent isocyanate derivatives are capable of irreversibly deactivating the proteolytic enzyme human leukocyte elastase (HLE). The inhibitors of this invention have been found to bond to primary specificity sites to thereby irreversibly eliminate enzyme activity.

Pulmonary emphysema is a disease characterized by alterations in the physiological lung function related to the loss of elastic recoil There is an uncontrolled degradation of lung connective tissue coincident with the development of emphysema.

It has been hypothesized that the development of emphysema stems from a proteinase proteinase-inhibitor imbalance. Human alpha-1-proteinase inhibitor (alpha-1-PI) is a defense protein that controls that activity of proteolytic enzymes, and that of HLE in particular. The inhibitory activity of alpha-1-PI is drastically reduced when the reactive site methionine residue is oxidized to the sulfoxide form by exogenous oxidants such as ozone, oxidants in cigarette smoke, or oxygen derived endogenous oxidants. The resulting proteinase proteinase-inhibitor imbalance often results in uncontrolled degradation of lung connective tissue. Accordingly, an ideal inhibitor of HLE would embody both inhibitory and anti-oxidant activity.

It is known that aliphatic isocyanates can be used to selectively inhibit serine proteinases. However the high toxicity of isocyanates renders them undesirable from a pharmacological standpoint There are, however, certain compounds known to function as latent isocyanates which do not possess high toxicity.

Selective inhibition is necessary so that an inhibitory agent will not affect closely related proteinases. Although HLE, cathepsin G, porcine pancreatic elastase (PPE) and alphachymotrypsin have many common features, such as similar catalytic apparatus, and extended binding site and a preference for hydrophobic substances (or inhibitors), they differ from each other in their substrate specificities. These diferences in substrate preference arise from variations in the size of the binding cleft at the catalytic sites. Studies have shown that PPE can accommodate small hydrophic side chains at its primary specificity site $S_1$. The $S_2$–$S_4$ subsites of PPE are similar to those of HLE while $S_1$ subsite of HLE is larger, enabling the accommodation of larger side chains at $S_1$. The N-terminal of HLE is homologous to that of PPE.

It was reported in *Biochemical and Biophysical Research Communications*, Vol. 45, No. 4, Pages 1890–94 (1980) that certain imidazole-N-carboxamides actively inhibited PPE. Specifically, the n-butyl derivative was found to be particularly capable of binding to the active site of the enzyme. These compounds were known to dissociate into isocyanates and imidazole under very mild conditions. Such compounds however were not found to be effective with HLE.

Subsequently it was reported at the American Chemical Society Division of Medicinal Chemistry, 183rd ACS National Meeting, Mar. 28–Apr. 2, 1982, that irreversible inhibition of PPE by amino acid derivative imidazole-N-carboxamides had been discovered. Particularly active were those derived from DL-norvaline and L-valine methyl esters. The inhibitor derived from glycine ethel ester however was found to be inactive; while that derived from D-valine methyl ester exhibited marginal activity. It was speculated that the compounds functioned via an enzyme induced generation of an isocyanate moiety at the active sight of the enzyme.

The interaction of a serine proteinase with alpha-1-PI results in the formation of a highly stable 1:1 complex involving the active site serine of the proteinase and a methionine-serine peptide bond in the alpha-1-PI. When the critical methionine residue at the active site of the alpha-1-PI is oxidized to the corresponding sulfoxide, the proteinase inhibitor is inactivated, creating an imbalance.

It has been discovered, however, that certain amino-acid-derived azolides are effective inhibitors of HLE, but not of PPE. These compounds may be effective based upon the fact that the active site of HLE is hydrophobic and prefers a valine, norvaline or norleucine residue at its $S_1$ subsite. Certain additional compounds have been found to be effective against HLE but only weakly effective against PPE.

Because HLE prefers hydrophobic substrates, potential inhibitors had been chosen based upon this important fact. Consequently, inhibitors reported were highly hydrophobic with limited solubility in aqueous media. It has now been discovered, however, that sulfonate salts of certain amino acids and related compounds demonstrate for the first time that ionic compounds can function as inhibitors of HLE. While it is not known with certainty, it is believed that the group bearing the charge must be disposed on the leaving group side. It is likely that the sulfonate group is not occupying the $S_1$ site, but rather is pointed away from the surface of the enzyme and toward the aqueous milieu.

Accordingly, these ionic derivatives of the methyl esters of L-valine, L-norvaline, and L-norleucine were found to be very potent inhibitors. In addition, the sulfonate salts of methyl esters of L-leucine, L-methionine and L-phenylalanine also inactivate HLE, but not as efficiently.

Isocyanates effective against serine proteinases have the following formula:

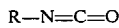

wherein R is a hydrophobic hydrocarbon group. Latent or blocked isocyanates of this invention have the following general formula:

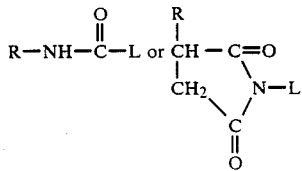

wherein the blocking group L is, as will be subsequently described, a reactive moiety which functions as an antioxidant and/or antiinflamatory agent in vivo.

Representative L groups which have been identified as effective groups include imidazole, $SO_3^-$, $OSO_2CH_3$, N-hydroxy succinimide and 2-pyridone. Representative hydropholic R groups which have been identified as effective in binding to the active site in HLE include certain amino acid derivatives, substituted or unsubstituted aralkyl groups, and certain sulfur containing amino acid esters.

Accordingly, it is an object of this invention to provide pharmaceutically effective inhibitory compounds for HLE.

It is another object of this invention to provide pharmaceutically effective inhibitory compounds which exhibit both inhibitory and anti-oxidant activity.

It is another object of this invention to provide amino acid derivatives and related compounds which either function as latent isocyanates or as ionic compounds derived from isocyanates which will irreversibly inhibit the enzymatic activity of HLE.

These and other objects will become readily apparent with reference to the following description.

As noted above, in recent years attempts to map the active sites of certain proteolytic enzymes have proven successful. This work paved the way for the development of irreversible and reversible inhibitors that can discriminate between individual members of this class of enzymes. These studies have demonstrated that properly designed small organic molecules can be used to inhibit selectively individual serine proteases, even though these molecules cannot participate in secondary subsite interactions.

It has previously been shown that aliphatic isocyanates can be used to inhibit selectively the serine proteases. However, the high toxicity of isocyanates has prompted investigation into the inhibitory activity of compounds that function as latent isocyanates. Certain azolides of the formula identified below derived from appropriate amino acid esters have been found to irreversibly inhibit both PPE and HLE and demonstrate that masked isocyanates can be used as inhibitors.

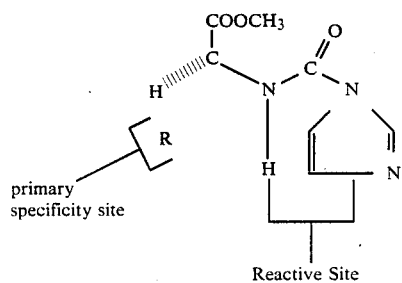

In addition to the amino acid derivatives identified above compounds having the following structures have been shown to be effective against HLE:

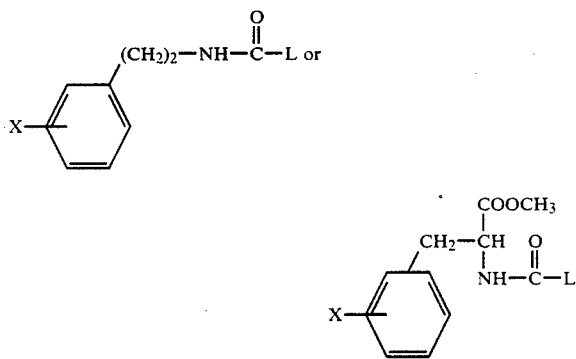

wherein X=H or CF$_3$, and L=imidazole, SO$_3^{-1}$K$^+$, N-hydroxy succinimide and 2-pyridone.

Further effective compounds were identified by the following structure:

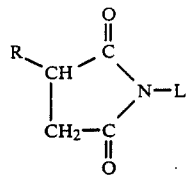

wherein R=alkyl or aryl, and L=OSO$_2$R.

Finally, compounds having the following structure were also found to be effective:

R—CH—(COOCH$_3$)—NH—CO—L wherein R is a sulfur containing amino acid dertivative and L=imidazole or SO$_3^-$K$^+$ The compounds of this invention and related compounds also evaluated, as will be subsequently described, were synthesized using known techniques The following are examples:

1. L-N-(Imidazol-1-ylcarbonyl)norvaline Methyl Ester. A 1.36-g(0.02 mol) sample of imidazole was mixed with 3.14 g (0.02 mol) of L-norvaline methyl ester isocyanate in 20 mL of anhydrous ethyl ether under a nitrogen atmosphere. The reaction mixture was refluxed with stirring for two hours. Removal of the solvent in vacuo left a colorless oil which solidified upon refrigeration. The isolated solid was homogeneous by TLC(silica gel:ethyl acetate/chloroform, 1:1), melted at 86°-88° C., and was obtained in 96% yield (4.3 g). Anal. )C$_{10}$H$_{15}$N$_3$O$_3$)C, H, N.

2. m-(Trifluoromethyl)phenylalanine Methyl Ester Isocyanate. A 5.0 mL (0.042 mol) sample of trichloromethyl chloroformate was added to a mixture of compound m-(trifluoromethyl benzyl) phenylalanine methyl ester hydrochloride (8.51 g, 0.03 mol) in 75 mL of dry dioxane under nitrogen. The reaction mixture was refluxed overnight under an efficient hood and with use of a gas trap (300 mL of 20% aqueous NaOH). Removal of the solvent in vacuo, followed by vacuum distillation of the oily residue, yielded 6.9 g (84%) of pure isocyanate: IR (neat) 2300 cm$^{-1}$ (N=C=O), 1730 (C=O); NMR (CDCl$_3$/Me$_4$Si) 7.5 (s, 4 H) 4.4 (d, 1 H), 3.8 (s, 3 H), 3.2 (d, 2 H). Anal. (C$_{12}$H$_{10}$NO$_3$F$_3$) C, H, N, F.

3. N-(1H-Imidazol-1-ylcarbonyl)-m-(trifluoromethyl)phenylalanine Methyl Ester. A 2.73 -g (0.01 mol) sample of appropriate isocyanate was mixed with imidazole (0.68 g, 0.01 mol) in 20 mL of anhydrous ethyl ether under nitrogen. After the mixture was refluxed for 2 h, the solvent was evaporated in vacuo, leaving an oily residue (3.3 g, 97%). The oily material was homogeneous by TLC (silica gel/CHCl$_3$/EtOAc, 1:1) IR (neat) 3130 cm$^{-1}$ (NH), 1715 (C=O); NMR (CDCl$_3$/Me$_4$Si) σ 8.3 (t, 1 H), 7.2 (m, 6 H), 4.4 (t, 1 H), 3.7 (s, 3 H), 3.2 (q, 2 H). Anal. (C$_{15}$H$_{14}$N$_3$F$_3$O$_3$) C, H, N, F.

4. N-(Sulfocarbonyl)DL-m-(trifluoromethyl)-phenylalanine Methyl Ester, Monopotassium Salt. A 2.73 -g (0.01 mol) sample of appropriate isocyanate in 5 mL of dioxane was added to potassium metabisulfite (1.11 g, 0.01 mol) in 5 mL of water at room temperature. After the mixture was stirred overnight, the precipitated solid was collected by suction and washed thoroughly with acetone. Compound 6 was obtained in 92% yield (3.6 g): IR (KBr) 3600 cm$^{-1}$ (NH), 1710 (C=O); NMR (D$_2$O/DSS) $\sigma$ 7.6 (s, 4 H), 6.8 (d, 1 H), 4.6 (t, 1 H), 3.7 (s, 3 H), 3.2 (d, 2 H). Anal. (C$_{12}$H$_{11}$F$_3$NO$_6$KS) C, H, N, S.

5. L-Phenylalanine Methyl Ester Isocyanate. A 10.7 -g (0.05 mol) sample of L-phenylalanine methyl ester hydrochloride salt was mixed with 200 mL of a 13% phosgene solution in toluene and refluxed for 4 h. Caution: this reaction should be carried out under an efficient hood with a gas trap of 20% aqueous NaOH. Evaporation of the solvent in vacuo left an oily residue, which was vacuum distilled, yielding 8.97 g (88%) of a colorless oil: IR (neat) 2250 cm$^{-1}$ (N=C=O); 1735 (C=O); NMR CDCl$_3$/Me$_4$Si) $\sigma$ 7.3–6.8 (m, 5 H) 4.2 (t, 1 H), 3.5 (s, 3 H), 2.9 (d, 2 H). Anal. (C$_{11}$H$_{11}$NO$_3$) C, H, N.

6. N-(1H-Imidazol-1-ylcarbonyl)-L-phenylalanine Methyl Ester. A 1.94 -g (0.01 mol) sample of appropriate isocyanate was added to imidazole (0.68 g, 0.01 mol) in 10 mL of anhydrous THF under nitrogen. After refluxing for 2 h and removal of the solvent in vacuo, a viscous colorless oil was obtained (2.40 g, 88%), homogeneous by TLC (silica gel chloroform/ethyl acetate, 1:1): IR (neat) 1735 cm$^{-1}$ C=O); NMR (CDCl$_3$/Me$_4$Si) $\sigma$ 8.3 (s, 1 H), 7.0–7.5 (m, 5 H), 5.9 (s, 1 H), 5.0 (br s, 1 H), 3.7 (s, 3 H), 3.3 (m, 2 H). Anal. (C$_{14}$H$_{15}$N$_3$O$_3$) C, H, N.

7. N-(Sulfocarbonyl)-L-phenylalanine Methyl Ester, Monopotassium Salt. Appropriate isocyanate (4.1 g, 0.02 mol) in 10 mL of dry dioxane was added to potassium metabisulfite (2.22 g, 0.01 mol) in 10 mL of water with stirring. The precipitated product was collected and washed thoroughly with acetone to yield 3.6 g (92%) of pure product: IR (KBr) 3200 (NH), 1740 and 1700 (C=O), 1220 (SO$_3$-); NMR (Me$_2$SO—d$_6$/Me$_4$Si) 8.2 (d, 1 H), 7.3 (s, 5 H), 4.5 (q, 1 H), 3.7 (s, 3 H), 3.15 (d, 2 H). Anal. (C$_{11}$H$_{12}$SO$_6$NK) C, H, N, S.

8. N-[2(1H-Pyridon-1-ylcarbonyl]-L-phenylalanine Methyl Ester. A mixture of appropriate isocyanate (1.02 g, 5 mmol) and 2-pyridone (0.48 g, 5 mmol) in 5 mL of dioxane was refluxed for 2 h. Removal of the solvent in vacuo left a viscous oil (1.4 g, 93%): IR (neat) 1720 cm$^{-1}$ C=O); NMR (CDCl$_3$/Me$_4$Si) $\sigma$ 8.3 (d, 1 H), 7.2 (s, 7 H), 6.5 (d, 1 H), 4.8 (t, 1 H), 3.6 (s, 3 H), 3.1 (d, 2 H). Anal. (C$_{16}$H$_{16}$N$_2$O$_4$) C, H, N.

9. N-(Succinimid-1-ylcarbonyl)-L-phenylalanine Methyl Ester. A 1.02 -g (5 mmol) sample of appropriate isocyanate and 0.58 g (5 mmol) of N-hydroxysuccinimide were refluxed in 5 mL of dioxane for 2 h. Evaporation of the solvent left a viscous oil (1.52 g, 95%): IR (neat) 3300 cm$^{-1}$ (NH br), 1770 (C=O); 1725 (C=O) NMR (CDCl$_3$/Me$_4$Si) $\sigma$ 7.3 (s, 5 H), 4.5 (d, 1 H), 3.7 (s, 3 H), 3.2 (d, 2 H), 2.8 (s, 4 H). Anal. (C$_{15}$H$_{16}$N$_2$O$_6$) C, H, N.

10. N-(1H-Imidazol-1-ylcarbonyl)-2-phenylalanine. A 2.94 -g (20 mmol) sample of 2-phenylethyl isocyanate and imidazole (1.36 g, 20 mmol) in 20 mL of dioxane were refluxed under nitrogen for 2 h. Removal of the solvent in vacuo left a white residue, which was recrystallized from CH$_2$Cl$_2$/hexane to give 3.7 g (86%) pure product: mp 101°–103° C.; IR (KBr) 3200 cm$^{-1}$ (NH), 1700 (C=O); NMR (CDCl$_3$/Me$_4$Si) $\sigma$ 8.1 (t, 1 H), 7.8 (s, 1 H), 7.3 (s, 1 H), 7.1 (s, 5 H), 6.7 (s, 1 H), 3.3 (t, 2 H), 2.7 (t, 2 H). Anal. (C$_{12}$H$_{13}$N$_3$O) C, H, N.

Succinimido N-(2-Phenylethyl) carbamate. A 2.94 -g (0.02 mol) sample of 2-phenylethyl isocyanate, 2.30 g (0.02 mol) of N-hydroxysuccinimide, and 20 mL of dioxane were refluxed under nitrogen for 2 h. Removal of the solvent left a solid residue, which was recrystallized from Ch$_2$Cl$_2$/hexane to yield 4.62 g (88%) pure product: mp 138°–139° C.; IR (KBr) 3260 cm$^{-1}$ (NH), 1730 (C=O, br); NMR (CDCl$_3$/Me$_4$Si) 7.3 (s, 5 H), 5.6 (br s, 1 H), 3.4 (q, 2 H), 2.8 (t, 2 H), 2.7 (s, 3 H). Anal. (C$_{13}$H$_{14}$N$_2$O$_4$) C, H, N.

12. 1[(2-Phenylethyl)carbamoyl]2(1H)-pyridone. A 2.94 -g (20 mmol) sample of 2-phenylethyl isocyanate and 1.90 g (20 mmol) of 2-pyridone in 20 mL of dioxane were refluxed for 2 h. Recrystallization of the solid residue yielded 4.2 g (87%) of product: mp 52°–53° C.; IR (KBr) 3100 cm$^{-1}$ (NH br), 1700 and 1650 (C=O); NMR (CDCl$_3$/Me$_4$Si) $\sigma$ 8.3 (d, 1 H), 7.2 (s, 6 H), 6.4 (d, 1 H), 6.2 (d, 1 H), 3.5 (t, 2 H), 2.7 (t, 2 H). Anal. (C$_{14}$H$_{14}$N$_2$O$_2$) C, H, N.

13. Potassium Oxol[(2-phenylethyl) amino]methanesulfonate Salt. 2-Phenylethyl isocyanate (2.94 g, 20 mmol) in 10 mL of dioxane was mixed with potassium metabisulfite (2.22 g, 10 mmol) in 10 mL of water and the mixture stirred overnight. The precipitated solid was collected by suction and washed with acetone. A 5.13 -g (96%) sample of pure salt was obtained: IR (KBr) 3300 cm$^{-1}$ (NH), 1660 (C=O); NMR (Me$_2$SO-d$_6$) $\sigma$ 7.3 (s, 5 H), 3.5 (t, 2 H), 2.8 (t, 3 H). Anal. (C$_9$H$_{10}$NSO$_4$K) C, H, N, S.

14. 2-Benzylsuccinic anhydride 10.0 g of 2-Benzyl succinic acid was mixed with 10 ml acetic anhydride and refluxed for 30 min. Removal of the solvent in vacuo left a crude solid which was triturated with n-penate and collected by suction filtration to give 8.4 g (91%) yield) anhydride, mp 95°–97° C. (A starting material for producing the following compound).

15. 3-Benzyl-N-benzyloxysuccinimide. Benzyloxyamine (5.41 g; 0.044 mol) in 17 ml toluene was added to a boiling solution of 2-Benzylsuccinic acid anyhdride (8.25 g; 0.043 mol) in 37 ml toluene. The solution was refluxed for 15 min. The solution was allowed to cool slowly, whereupon a solid crystallized (7.60 g; 60% yield), mp 130°–2° C. IR (KBr): 1690 cm$^{-1}$ (C=O). NMR (DMSO-d$_6$/CDCl$_3$): $\sigma$ 7.3–7.2 (10H), 4.7 (s 2 H) 2.8-2.3 (br 5 H).

16. 3-Benzyl-N-hydroxysuccinimide. 3.0 g of compound 18 in 100 ml methanol-ethanol (1:1) was hydrogentated in the presence of 1 g 10% Pd-C over a period of 4 h. Celite was added and the mixture was filtered. Evaporation of the solvent in vacuo left a viscous oil. Toluene (50 ml) was added and the solution refluxed briefly using a Dean-Stark separator. Evaporation of the solvent left a white solid (1.96 g; 96%), mp 120°–1° C. IR (KBr): 3200 (OH), 1760 and 1690 cm$^{-1}$ (C=O) NMR (DSMO-d$_6$): $\sigma$ 7.9 (br, 1 H), 7.05 (s, 5 H), 2.8-2.2 (m, 5 H).

17. (dl)-3-Benzyl-N-(methanesulfonyloxy) succinimide. A solution of 3-Benzyl-N-hydroxysuccinimide (2.0 g; 0.01 mol) and pyridine (1.58 g; 0.02 mol) in 10 ml dry toluene was kept at 40° C. under a nitrogen atmosphere while methanesulfonyl chloride (1.14 g; 0.01 mol) was added dropwise. Stirring was continued for 2 h at 50° C. The solution was cooled, water (15 ml) was added and the solution extracted with ethyl acetate (3×25 ml). The solution was dried with anhydrous sodium sulfate, filtered and evaporated in vacuo, leaving behind a white solid (2.3 g; 80%), mp 70°–71° C. IR (KBr): 1790 and 1725 (C=O). NMR (CDCl$_3$): $\sigma$ 7.3 (d, 5 H), 3.4 (s, 2 H), 3.15-2.1 (m, 5 H)

IN VITRO INHIBITION MEASUREMENTS

The enzyme assays used to evaluate the potency of the inhibitors in vitro were performed as follows: PPE was assayed spectrophotometrically at 347.5 nm with (tert-butoxycarbonyl)-alanyl-p-nitrophenol in 0.05 M phosphate buffer, pH 6.5, 25° C., or by using succinyl-L-trialanyl-p-nitroanilide in 0.1 M Tris buffer, pH 8.0, at 410 nm. HLE was assayed spectrophotometrically at 410 nm with succinyl-L-trialanyl-p-nitroanilide or methoxy succinyl ala-ala-pro-val-p-nitroanilide (As describe by K. Wakajima et al in the J. Biol. Chem, 254, 4027–4032 (1979) and T. Teshima et al, in J. Biol. Chem 257, 5085–5091 (1982). The potency of an inhibitor is determined by obtaining a kinetic determination of the bimolecular rate constant $K_3/K_i$ (or $R_{obsd}/[I]$). The HLE used in these studies may be obtained from Elastin Products, St. Louis, Mo.) in 0.1 M Tris buffer, pH 8.0.

The appropriate amount of inhibitor in acetonitrile was mixed with PPE in phosphate buffer solution and placed in a constant temperature bath. Aliquots were withdrawn at different time intervals and transferred to a cuvette containing 100 uL of substrate, 140 uL of acetonitrile, and 2 mL of phosphate buffer, pH 6.5. After incubating for 30 seconds, the absorbance change was monitored for two minutes at 347.5 nm. The inhibitor-to-enzyme ratios varied between 50 and 200, and the incubation intervals were shortened or lengthened depending upon the potency of the inhibitor. Controlled reactions for 100% PPE activity were run in the presence of acetonitrile. A similar procedure was followed for HLE.

The reaction of an irreversible inhibitor with PPE and HLE may be illustrated by the scheme shown below:

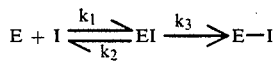

where EI is the noncovalently bound enzyme-inactivator complex and E-I is the final product with the inhibitor covalently bound to the enzyme. The kinetics data were analyzed according to known procedures. The apparent pseudo-first-order inactivation rate constants were determined from the slopes of semilogarithmic plots of enzymatic activity remaining versus time using the following equation:

$$\ln(E_t/E_0) = k_{obsd} t$$

where $E_t/E_0$ is the amount of active enzyme remaining after time "t". Inhibition is generally expressed in terms of $k_3/K_i$, $M^{-1}s^{-1}$, wherein $K_i$ is the disassociation constant for the enzyme inhibitor complex and $k_3$ is a limiting rate constant for the irreversible loss of enzymatic activity.

Table I below illustrates the inhibition found with assays of nine amino-acid-derived azolides against PPE and HLE.

TABLE I

| Compd | R | Porcine pancreatic elastase $k_3/K_i$ $M^{-1}s^{-1}$ | Human leukocyte elastase $k_3/K_i$ $M^{-1}s^{-1}$ |
|---|---|---|---|
| 1 | H | | |
| 2 | L-CH$_3$ | | |
| 3 | L-(CH$_3$)$_2$CH | 2.8 | 193 |
| 4 | D-(CH$_3$)$_2$CH | | |
| 5 | L-CH$_3$CH$_2$CH$_2$ | 6.3 | 500 |
| 6 | D-CH$_3$CH$_2$CH$_2$ | | |
| 7 | L-(CH$_3$)$_2$CHCH$_2$ | 0.5 | |
| 8 | L-CH$_3$CH$_2$CH(CH$_3$) | 1.0 | |
| 9 | DL-CH$_3$CH$_2$CH$_2$CH$_2$ | 2.2 | 167 |

With attention to Table I above, the glycine derivative, Compound 1, failed to deactivate either PPE or HLE. Compound 2 showed marginal inhibitory activity, but the valine derivative, Compound 3, was found to be an excellent inhibitor against HLE and a poor inhibitor of PPE. As anticipated, the corresponding D-isomer, Compound 4, had no effect on either PPE or HLE, reflecting unproductive binding and/or wrong stereochemical alignment of the inhibitor reactive site and the catalytic residues. HLE apparently shows a preference for a 3 or 4-carbon straight alkyl chain at the $P_1$ site and, accordingly, the norvaline derivative, Compound 5, and the norleucine derivative, Compound 9, were found to be effective inhibitors of HLE. Thus, Compounds 3, 5, and 9 show an avidity for HLE, but little for PPE.

In addition to the compounds evaluated above, a methionine derivative, N-(1H-imidazol-1-ylcarbonyl)-methionine methyl ester, was evaluated. This compound exhibited a remarkable specificity and high potency toward HLE, but PPE was unaffected by the inhibitor under the same conditions. While it is not intuitively apparent why such a high specificity is shown by the methionine derivative, it is likely that the side chain of methionine is highly complementary to the $S_1$ subsite of HLE. Steric effects probably play a large role as far as the lack of inhibitory activity toward PPE is concerned. This finding is of pharmaceutical significance since the isosteric replacement of a $CH_2$ by sulfur gives rise to a highly biospecific inhibitor.

As noted above, the foregoing derivatives are hydrophobic and, therefore, only weakly soluble in aqueous solution. It has been discovered, however, that excellent inhibitory activity against HLE can be exhibited with ionic compounds.

Monopotassium salts were produced by admixing the appropriate amino acid ester isocyanate and an aqueous solution of potassium metabisulfite in dioxane. The monopotassium sulfonate salts had the following formula:

Table II below summarizes the results of enzyme assays against HLE for each of the enumerated compounds. The assay procedure used was the procedure identified relative to the tests above in Table I.

TABLE II

| Compound | Precursor Amino Acid | R | $k_2/K_i$ $M^{-1}sec^{-1}$ |
|---|---|---|---|
| 1 | Gly | H | inactive |
| 2 | L-Ala | CH$_3$ | inactive |
| 3 | L-Val | (CH$_3$)$_2$CH | 800 |
| 4 | L-Norval | CH$_3$CH$_2$CH$_2$ | 860 |
| 5 | D-Norval | CH$_3$CH$_2$CH$_2$ | inactive |

TABLE II-continued

| Compound | Precursor Amino Acid | R | $k_2/K_i$ $M^{-1}sec^{-1}$ |
|---|---|---|---|
| 6 | L-Norleu | $CH_3CH_2CH_2CH_2$ | 920 |
| 7 | L-Leu | $(CH_3)_2CHCH_2$ | 260 |
| 8 | L-Met | $CH_3SCH_2CH_2$ | 260 |
| 9 | L-Phe | $PhCH_2$ | 530 |

To summarize, the sulfonate salts of L-valine, L-norvaline, and L-norleucine methyl esters proved to be very potent inhibitors of HLE. In addition, the derivatives of L-leucine, L-methionine, and L-phenylalamine also deactivate HLE but were not as effective. This is in agreement with what is presently known about the primary specificity site ($S_1$ subsite) of HLE. The active site of HLE is hydrophobic and prefers a valine, norvaline, or norleucine residue at its $S_1$ subsite. In further tests, for example, L-norvaline had no effect on chymotrypsin and PPE under comparable conditions, attesting to the high specificity of the inhibitor. Thus, selective inhibition can be achieved by manipulating the side chain that binds to the $S_1$ subsite of each serine proteinase, since the topographical features of the active sites of the various serine proteases are known to be different. As expected, the inhibitor derived from D-norvaline methyl ester showed no inhibitory activity toward HLE. The compounds derived from glycine and L-alanine were also devoid of any inhibitory activity. The lack of inhibitory activity of these compounds can be ascribed to poor binding. Accordingly, the amino acid sulfonate salts of this invention demonstrate that ionic compounds can function as inhibitors of HLE provided the group bearing the charge is on the leaving-group side. As noted above, it is unlikely that the sulfonate group occupies the $S_1$ subsite. It is likely that this group is pointing away from the surface of the enzyme and toward the aqueous milieu. The high potency and specificity exhibited by these inhibitors, as well as their ease of preparation, render them highly useful as enzyme probes and pharmacological agents.

Tables III and IV below summarize in vitro tests with compounds wherein an aromatic ring, either substituted or unsubstituted is used to bind to the $S_1$ subsite of HLE.

TABLE III

Inhibition of Leukocyte Elastase by Azolides, Sulfonate Salts, and Other Related Compounds

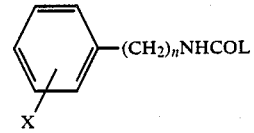

I

| compd[a] | mp, °C. | X | n | L | $k_{obsd}/[I]$, $M^{-1}s^{-1}$ |
|---|---|---|---|---|---|
| 1 | 200 dec | H | 0 | $SO_3^-$ | inactive[b] |
| 2 | 225 dec | m-Cl | 0 | $SO_3^-$ | inactive[b] |
| 3 | 260 dec | p-Cl | 0 | $SO_3^-$ | inactive[b] |
| 4 | 200 dec | m-F | 0 | $SO_3^-$ | inactive[b] |
| 5 | 205 dec | o-$CF_3$ | 0 | $SO_3^-$ | inactive[b] |
| 6 | 186–188 | m-$CF_3$ | 0 | $SO_3^-$ | inactive[b] |
| 7 | 165 dec | p-$CF_3$ | 0 | $SO_3^-$ | inactive[b] |
| 8 | 107–108 | m-F | 0 | imidazole | inactive[b] |
| 9 | 162–164 | o-$CF_3$ | 0 | imidazole | inactive[b] |
| 10 | 80–82 | m-$CF_3$ | 0 | imidazole | inactive[b] |
| 11 | 130–132 | p-$CF_3$ | 1 | imidazole | inactive[b] |
| 12 | 240 dec | m-F | 1 | $SO_3^-$ | inactive[b] |
| 13 | 103–106 | m-$CF_3$ | 1 | $SO_3^-$ | inactive[b] |
| 14 | 102–104 | m-F | 1 | imidazole | inactive[b] |
| 15 | 84–86 | m-$CF_3$ | 1 | imidazole | inactive[b] |
| 16 | 270 dec | H | 2 | $SO_3^-$ | 4 |
| 17 | 265 dec | m-F | 2 | $SO_3^-$ | 18 |
| 18 | 101–103 dec | H | 2 | imidazole | 35 |
| 19 | 106–108 | m-F | 2 | imidazole | 38 |
| 20 | 85–87 | m-$CF_3$ | 2 | imidazole | 483 |
| 21 | 52–53 | H | imidazole | 2-pyridone | 500 |
| 22 | 76–78 | m-F | imidazole | 2-pyridone | 317 |
| 23 | 64–66 | m-$CF_3$ | imidazole | 2-pyridone | 11722 |
| 24 | 138–139 | H | imidazole | N-hydroxysuccinimide | 927 |
| 25 | 107–109 | m-F | imidazole | N-hydroxysuccinimide | 823 |
| 26 | 96–98 | m-$CF_3$ | imidazole | N-hydroxysuccinimide | 13500 |

[a]All compounds gave correct elementary analyses.
[b]No inhibition was observed when 243-fold excess of inhibitor over enzyme and 10-min incubation time were used under comparable conditions.

TABLE IV

Inhibition of Leukocyte Elastase by Derivatives of Phenylalanine

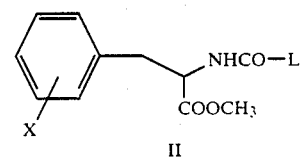

II

| compd[a] | mp, °C. | X | L | $k_{obsd}/[I]$, $M^{-1}s^{-1}$ |
|---|---|---|---|---|
| 27 | 127–130 | H | $SO_3^-$ | 550[b] |
| 28[a] | c | H | imidazole | 2070 |
| 29[a] | c | H | 2-pyridone | 2329 |
| 30[a] | c | H | N-hydroxysuccinimide | 6635 |
| 31 | 255 dec | m-F | $SO_3^-$ | 57 |
| 32 | 210 dec | m-$CF_3$ | $SO_3^-$ | 13 |
| 33 | c | m-F | imidazole | 318 |

TABLE IV-continued
Inhibition of Leukocyte Elastase by Derivatives of Phenylalanine Structure II: phenyl ring with X substituent, CH2-CH(NHCO-L)(COOCH3)

| compd[a] | mp, °C. | X | L | $k_{obsd}/[I]$, $M^{-1} s^{-1}$ |
|---|---|---|---|---|
| 34 | c | m-CF3 | imidazole | 1096 |

[a]All compounds gave correct elementary analyses.
[b]Compounds derived from L-phenylalanine methyl ester. The remainder of the compounds were made from DL-m-fluoro- and DL-m-(trifluoro-methyl)phenylalanine methyl esters.
[c]Oil.

As may be expected, activity varied widely depending upon the nature of X, L and n. As is evident, active compounds only were obtained when n=2 and no inhibition was observed when n=0 or 1.

As shown above, a variety of latent isocyanates can function as inhibitors of HLE. Furthermore, the affinity of the hydrophobic aromatic group was found to increase in the presence of a CF3 substituent group.

Table V below summarizes in vitro tests on certain succinimide derivatives.

TABLE V
INHIBITION OF LEUKOCYTE ELASTASE BY DERIVATIVES OF (dl)-3-BENZYL-N-HYDROXYSUCCINIMIDE I

Structure I: succinimide ring with R-CH, CH2-C, N-L

| R | L | $k_{obsd}/[I]$ $M^{-1} s^{-1}$ |
|---|---|---|
| BENZYL | —OSO2CH3 | 1170[a,b] |
| " | —OSO2—(CH2)3CH3 | 1680 |
| " | —OSO2—(CH2)7CH3 | 1273 |
| " | —OSO2—N(CH3)2 | 323 |
| " | —OSO2—phenyl | 1171 |
| " | —OSO2—C6H4—Br | 1648 |
| " | —OSO2—C6H4—CH3 | 1608 |
| " | —OH or —OCH2—phenyl | inactive |
| H | —OSO2—CH3 | inactive |

TABLE V-continued
INHIBITION OF LEUKOCYTE ELASTASE BY DERIVATIVES OF (dl)-3-BENZYL-N-HYDROXYSUCCINIMIDE I

| R | L | $k_{obsd}/[I]$ $M^{-1} s^{-1}$ |
|---|---|---|
| H | —OSO2—C6H4—CH3 | inactive |

[a]alpha-Chymotrypsin was also efficiently inactivated with a $k_{obsd}/[I] = 9000\ M^{-1} s^{-1}$.
[b]Porcine pancreatic elastase was unaffected.

The results of in vitro studies using amino acid derived azolides and sulfonate salts having a thioether side chain are summarized in Table VI below. The inhibition of HLE by these compounds was, as in the case of the above compounds, time dependent and irreversible. As shown in Table VI, azolides are much more effective in inhibiting HLE then the corresponding sulfonate salts, although the latter possess superior physical properties. The corresponding sulfoxides (compounds 2 and 4) were found to be inactive. The greatly diminished protease inhibitory activity of the compounds with bulky and/or less hydrophobic side chains reflects the known substrate specificity of the enzyme.

TABLE VI.
Inhibition or HLE by Azolides and Sulfonate Salts or Sulfur-containing Amino Acid Esters and Related Compounds.
R—CH(COOCH3)—NH—CO—L

| Compound | R. | L | $k_{obsd}/[I]$ $M^{-1} sec^{-1a}$ |
|---|---|---|---|
| 1 | (L)-CH3SCH2CH2— | SO3−K+ | 260 |
| 2 | (L)-CH3SOCH2CH2— | " | inactive |
| 3 | (L)-CH3CH2SCH2— | " | 1800 |
| 4 | (L)-CH3CH2SOCH2— | " | inactive |
| 5 | (L)-CH3SCH2— | " | 1508 |
| 6 | (L)-PhCH2SCH2— | " | inactive |
| 7 | (L)-(-CH2—S—S—CH2—) | " | inactive |
| 8 | (L)-CH3OOC—CH2SCH2— | " | 17 |
| 9 | (L)-CH3SCH2— | Imidazole | 4049 |
| 10 | (L)-CH3CH2SCH2— | " | 4228 |
| 11 | (L)-CH3OOC—CH2SCH2— | " | 15 |
| 12 | (L)-CH3CH2CH2— | " | 500 |

[a]The apparent pseudo-first-order inactivation rate constants ($k_{obsd}$) were determined by plotting in [E]$_t$/[E]o vs time.

In addition, compound 3, Table VI, was exposed to oxidants in vitro and the rates of its inactivation with chloramine-T and H2O2 compared to buffer alone are summarized in Table VII below. Both oxidants are scavenged by the inhibitor in a time dependent and efficient fashion. Table VII indicates that the inhibitor undergoes hydrolysis in buffer solution (pH 8.0) with a half life of twenty minutes. With the addition of oxidants shorter half lives were observed. The observed rates of inhibitor inactivation are 6 to 12 fold smaller than the rate at which the inhibitor inactivates the enzyme.

TABLE VII.

Inactivation of S-ethylcysteine Sulfonate Salt
(compound 3, Table VI) by Oxidants.

| Oxidant, [Concentration] | $k_{obsd}$ sec$^{-1}$ |
|---|---|
| Triss buffer, pH 8.0 (0.2M) | $5.8 \times 10^{-4}$ |
| Chloramine T (0.06 mM) | $6.6 \times 10^{-4}$ |
| Chloramine T (0.06 mM) | $3.2 \times 10^{-3}$ |
| H$_2$O$_2$ (1 mM) | $1.2 \times 10^{-3}$ |

IN VIVO TESTS

The L-norvaline azolide, Compound 5, Table I, and the methyl ester Compound 12, Table VI were also evaluated in vivo to verify in vitro activity.

Animal models of emphysema include intratracheal administration of an elastolytic protease (PPE, HLE or papain) to cause a slowly progressive, destructive lesion in the lung. These proteases induce a lesion that is evident in the first few hours.

The method used for in vivo evaluation involved injection of a test solution into the trachea, or directly into one bronchus. In general, the method of Hayes et al *J. Pathol,* 117, 1-14 (1975) was used. A fine teflon tubing was connected to a pipette and inserted into the trachea after the animals were lightly anesthetized by IP injection. The contents of the pipette were then ejected. It was previously determined that instillation of 20 ul of a dye solution resulted in staining about one half of the left or right lower lobe, resulting in localized lobar instillation. It was further determined that instillation of 40 ug of PPE in the same volume causes an unambigous emphysematous lesion which is restricted to the instilled lobe. After 7 to 10 days to allow inflamation to subside, the animals were sacrificed followed by exsanguination via the descending aorta. PPE was used rather than HLE to produce the lesion because emphysema developes over a much shorter period of time. Emphysema then was induced under acute condition so that the effects of the compounds tested could be investigated under the time constraints of a laboratory procedure. PPE with an animal model has been used in research in the past to study other, unrelated, inhibitors. (Bergeson, S. H. et al., European Patent No. 0189305 (1986).

It is important to note that the compounds studied in vivo are much more effective in inhibiting HLE than PPE in vitro. Therefore, the dosage levels with HLE would be expected to be much lower. The L-Norvaline methyl ester azolide evaluated below, for example, is about eighty times more effective against HLE than PPE. Thus, if the inhibitor can block the formation of an emphysematous lesion caused by PPE, it would be expected that the compound would accomplish the same thing with HLE.

Initially, the tolerance of 30-40 gram male ICR mice to intraperitoneal (IP) or intratracheal (IT) injection of inhibitor (Compound 5, Table I) was evaluated. Table VIII below summarizes the results thereof:

TABLE VIII.

| Treatment | Volume | Survival | Total Inhibitor Injected |
|---|---|---|---|
| IP 20% DMSO | 2.0 ml | + | 0 |
| IP 20% DMSO + 0.02M Inhibitor | 2.0 ml | + | 40 umoles |
| IP 100% DMSO | 0.02 ml | + | 0 |
| IP 100% DMSO + 2.0M Inhibitor | 0.02 ml | + | 40 umoles |
| IT Saline + | 0.02 ml | + | 0 |
| 5% DMSO | | | |
| IT Saline + 5% DMSO + 0.05M Inhibitor | 0.02 ml | + | 1 umole |

As can be seen above, all animals survived and no animals showed abnormal pulmonary pathology.

Animals were also used to evaluate the effect of simultaneous intratracheal installation of PPE with the above inhibitor compound. The ICR mice in this experiment were used to evaluate the effect of the inhibitor in preventing emphysema induction. Table IX below illustrates the results of these tests:

TABLE IX.

| Treatment | Inhibitor | Emphysema |
|---|---|---|
| IT 34 ug PPE | 0 | Yes |
| IT 0 | 1 umole | No |
| IT 34 ug PPE | 1 umole | No |

All animals were sacrificed ten days after instillation. As can be seen, the inhibitor prevented emphysema when given simultaneously with PPE. Therefore, the free functional enzyme did not dissociate in vivo.

The L-Norvaline azolide ethyl ester, Compound 12, Table VI, was also evaluated in vivo with the results set forth in Table X below. It should be noted that all mice treated tolerated all doses of the inhibitor. In view of the fact that two tenths umoles of inhibitor is 100 times of the amount of the inhibitor necessary to inhibit the 40 ug of elastase in vitro, dosages were kept in the range of 1 to 10 umoles of inhibitor. Because PPE was used and the inhibitor is much more effective against HLE than PPE, if HLE is used the dosage level could be lower.

TABLE X.

Protection Against Elastase-induced Emphysema by
(L)-Norvaline Azolide Methyl Ester (compound 12,
Table VI) in the Mouse.

| umoles Inhibitor | Inhibitor Treatment Prior to Elastse* | n | Mouse Lung Histology | |
|---|---|---|---|---|
| | | | Normal | Emphysematous |
| 0 | No elastase | 4 | 4 | 0 |
| 0 | + Elastase | 5 | 1 | 4 |
| 10 | No elastase | 7 | 7 | 0 |
| 10 | 3 hr, then elastase | 2 | 0 | 2 |
| 10 | 2 hr, then elastase | 6 | 0 | 6 |
| 10 | 1 hr, then elastase | 7 | 2 | 5 |
| 5 | 30 min. then elastase | 3 | 3 | 0 |
| 1 | Simultaneous admin. | 4 | 4 | 0 |

*Elastase: 20 ul containing 40 ug pancreatic elastase

As noted above, the method of in vivo testing is a modification of that of Hayes et al. However, the test solutions are inserted past the vocal chords into one bronchus by resistance. It was established initially that 20 ul of a solution of PPE (2 milligrams per milliter in saline) would create a reliable and unambigous emphysematous lesion. It should also be noted that the animals were scored for the presence of absence of such a lesion in any lobe without regard to the severity of the lesion.

The inhibitor was found to block the effects of PPE in the animal model used and to be devoid of any toxic side effects. While it is not known for certain, it is believed that when the compound interacts with HLE, inhibiting the enzyme irreversibly, imidazole is released into the surrounding medium. This latter is a known antiimflammatory agent and an inhibitor of thromboxane synthetease. It should be noted that the nature of the precursor amino acid and the moiety that is released into the surrounding medium then can be selected, provided the inhibitory activity is retained.

To summarize, it has been discovered that azolide derivatives of certain amino acids and the sulfonate salts thereof are highly specific inhibitors for HLE and, therefore, are useful pharmacological agents in the prevention of the HLE imbalance which results in emphysema. The L-valine, L-norvaline, and L-leucine and methionine azolides proved to be highly effective. In addition, the L-valine, L-norvaline, L-norleucine, and L-leucine, L-methionine and L-phenylalamine sulfonate salts also proved to be effective inhibitors of HLE. Related alkyl amino acids proved to be ineffective.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A compound having the formula:

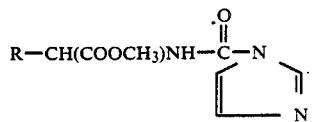

wherein R is a member selected from the group consisting of L $(CH_3)_2CH-$; L $CH_3-CH_2-CH_2-$; DL $CH_3-CH_2-CH_2-CH_2$; L$(CH_3)_2 CH-CH_2-$; and L $CH_3-CH_2-CH-(CH_3)_2$.

* * * * *